United States Patent
White et al.

(10) Patent No.: US 6,656,184 B1
(45) Date of Patent: Dec. 2, 2003

(54) BONE SCREW WITH HELICAL SPRING

(75) Inventors: John R. White, Winona Lake, IN (US); Jeffrey C. King, Columbia City, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 10/042,959

(22) Filed: Jan. 9, 2002

(51) Int. Cl.[7] .................. A61B 17/56; A61B 17/58; A61F 2/30
(52) U.S. Cl. ............................ 606/73; 606/71
(58) Field of Search ............... 606/59, 61, 65, 606/71, 72, 73; 411/82.1, 392, 412, 413, 438

(56) References Cited

U.S. PATENT DOCUMENTS

| | | | |
|---|---|---|---|
| 2,397,545 A | | 2/1946 | Hardinge |
| 3,051,169 A | * | 8/1962 | Grath .................. 128/92 |
| 3,435,526 A | | 4/1969 | Brancato |
| 4,129,903 A | | 12/1978 | Huggler |
| 4,673,407 A | | 6/1987 | Martin |
| 4,947,502 A | | 8/1990 | Engelhardt |
| 4,959,064 A | | 9/1990 | Engelhardt |
| 4,986,834 A | | 1/1991 | Smith et al. |
| 4,990,161 A | * | 2/1991 | Kampner ............... 623/16 |
| 5,007,935 A | | 4/1991 | Vincent et al. |
| 5,035,712 A | | 7/1991 | Hoffman |
| 5,411,504 A | | 5/1995 | Vilas |
| 5,486,176 A | * | 1/1996 | Hildebrand et al. ......... 606/71 |
| 5,800,553 A | | 9/1998 | Alberktsson et al. |
| 5,951,160 A | * | 9/1999 | Ronk .................. 366/130 |
| 6,197,065 B1 | | 3/2001 | Martin et al. |
| 6,486,232 B1 | * | 11/2002 | Wise et al. ............ 523/118 |
| 2001/0021852 A1 | * | 9/2001 | Chappius ................ 606/73 |

* cited by examiner

Primary Examiner—Pedro Philogene
Assistant Examiner—Anuradha Ramana
(74) Attorney, Agent, or Firm—Harness, Dickey & Pierce, P.L.C.

(57) ABSTRACT

A bone screw, and method of using the same, are described. The bone screw includes (1) a distal threaded portion having a first orientation, (2) a proximal head portion, and (3) an intermediate portion including a compressive member, such as but not limited to a single or double helix, integral with the distal and proximal portions, wherein the compressive member has a second orientation opposite that of the first orientation. When a force (e.g., rotational or axial) is applied to the bone screw in the first direction, the spaces between the surfaces of the compressive member increase, due to the difference in orientation. In this stressed state, a resorbable material is then applied within the spaces and is allowed to cure. Once the bone screw is inserted into the bone member, the resorbable material will begin to be resorbed, whereupon the compressive member will relax and exert tension between the bone member and any other object the bone screw is secured to.

18 Claims, 4 Drawing Sheets

BONE SCREW WITH HELICAL SPRING

FIELD OF THE INVENTION

The present invention relates generally to bone screws, and more particularly, to a new and improved bone screw having an intermediate helical spring portion, wherein a resorbable material is disposed within the spaces of the helical spring portion when the bone screw is in a stressed state, so as to provide various rates of compliant fixation.

BACKGROUND OF THE INVENTION

The use of orthopedic fastening devices, such as bone screws, has greatly aided the medical field in the treatment of bone fractures, as well as enabling the ever increasing use of orthopedic implants and orthopedic appliances. With respect to the treatment of bone fractures, it is sometimes generally necessary to surgically reposition the fragmented bone members in an anatomically acceptable orientation, and then fasten the bone members together in order to facilitate the healing process. Bone screws are typically employed in stabilization procedures used to treat bone fractures.

When a bone screw is employed, either to fasten two or more bone members together or to secure an orthopedic appliance (e.g., bone plate) to a bone surface, and the bone screw is tightened, initially, tension in the screw is relatively very high, and holds the bone members together. However, bone is a viscoelastic material and undergoes a phenomenon known as stress relaxation immediately after torque has been applied to the bone screw. The stress relaxation response is quite pronounced and causes immediate and rapid reduction in the bone screw tension and, hence, the force holding the bone: members together. Furthermore, after a conventional bone screw is tightened, and the bone member is laterally displaced, as by bending, the rigidity of the bone screw causes the surrounding bone to fail because the bone has lower strength and stiffness than the bone screw. This can lead to failure of the fixation and eventual non-union or misalignment of the bone members at the fracture site.

One approach to overcoming this problem has been the use of dynamic tension bone screws. U.S. Pat. No. 4,959,064 to Engelhardt describes an example of a dynamic tension bone screw. A conventional bone screw, having a proximal head portion and a distal threaded shank, is modified by milling a length of the shank portion to remove the outermost peak of the threads formed on the shank. This results in an intermediate segment having a smaller diameter than the threaded shank. Next, an elongated bore is formed, symmetrical with the longitudinal axis of the bone screw and having a diameter slightly larger than the root diameter of the threads on the shank. This perforation of the surface of the bone screw in a spiral fashion along the thread root results in the formation of a tension spring. It should be noted that both the threaded shank and the tension spring are oriented in the same general direction (e.g., both are either "right-hand" oriented). The bore extends as far as the distal end member into which is suitably formed, symmetrical about a longitudinal axis of the bone screw, a tool receiving recess.

When it is desired to rejoin a pair of bone fragments, a pair of aligned bores are formed respectively in the two bone fragments. Thereupon, the modified bone screw is inserted into the first (i.e., proximal) bore, and a suitable tool, such as a hexagonal drive wrench, is inserted into the recess to rotate the distal end member around its longitudinal axis, and therefore, also the rest of the modified bone screw. With continued insertion of the modified bone screw, the distal end member eventually enters and advances along the second (i.e., distal) bore of the distal bone fragment. As the distal end member continues to advance along the distal bore, the head member moves into engagement with the outer surface of the proximal bone fragment such that continued advancement of the distal end member causes the spring to stretch beyond its relaxed condition (due to the spring having the same orientation as the threaded distal end member). As the bone fragments undergo stress relaxation, the modified screw similarly relaxes, while continuing to hold the fragments together due to the remaining tension in the spring portion.

While the modified bone screw described by Engelhardt was an improvement over conventional bone screws, with respect to conserving tension in the screw over time as stress relaxation occurred, there still exists a need for a new and improved bone screw, and method of making same, that combines the best feature of conventional bone screws, i.e., high initial tension in the bone screw, with the best feature of dynamic tension bone screws, i.e., conservation of moderate tension in the bone screw over time, while avoiding the worst feature of conventional bone screws, i.e., rapid decrease in tension in the bone screw over time, and the worst feature of dynamic tension bone screws, i.e., relatively lower initial tension in the bone screw as compared to conventional bone screws.

SUMMARY OF THE INVENTION

In accordance with a first embodiment of the present invention, a bone screw is provided, comprising (1) a distal portion having a threaded surface thereon, the threaded surface having a first orientation, (2) a proximal portion, and (3) an intermediate portion comprising a compressive member integral with said distal and proximal portions, the compressive member having a second orientation opposite that of the first orientation.

In accordance with a second embodiment of the present invention, a bone screw is provided, comprising: (1) a distal portion having a threaded surface thereon, (2) a proximal portion, (3) an intermediate portion comprising a compressive member integral with said distal and proximal portions, the compressive member having an area defining at least one space between adjacent surfaces of the compressive member, and (4) a resorbable material disposed within the at least one space of the compressive member.

In accordance with a third embodiment of the present invention, a bone screw is provided, comprising: (1) a distal portion having a threaded surface thereon, the threaded surface having a first orientation, (2) a proximal portion having a recess formed therein for receiving a member capable of permitting the insertion of the bone screw into a bone member, (3) an intermediate portion comprising a compressive member integral with said distal and proximal portions, the compressive member having a second orientation, the compressive member having an area defining at least one space between adjacent surfaces of the compressive member, and (4) a resorbable material disposed within the least one space of the compressive member when the compressive member is in a stressed state.

In accordance with a fourth embodiment of the present invention, a method of making a bone screw is provided, comprising: (1) providing a member, (2) forming a threaded surface on a distal portion of the member, the threaded surface having a first orientation, and (3) forming a compressive member adjacent to the threaded surface, the compressive member having a second orientation opposite that of the first orientation, wherein the compressive member has an area defining at least one space between adjacent surfaces of the compressive member.

In accordance with a fifth embodiment of the present invention, a method of making a bone screw is provided, comprising: (1) providing a member, (2) forming a threaded surface on a distal portion of the member, the threaded surface having a first orientation, (3) forming a compressive member adjacent to the threaded surface, the compressive member having a second orientation opposite that of the first orientation, the compressive member having an area defining at least one space between adjacent surfaces of the compressive member, and (4) applying a resorbable material onto the least one space of the compressive member.

In accordance with a sixth embodiment of the present invention, a method of securing a bone member to an adjacent member is provided, comprising: (1) forming at least one bore in the bone member, (2) providing a bone screw, (3) inserting the bone screw into the at least one bore. The bone screw includes a threaded surface on a distal portion thereof, the threaded surface having a first orientation, a compressive member adjacent to the threaded surface, the compressive member having a second orientation opposite that of the first orientation, the compressive member having an area defining at least one space between adjacent surfaces of the compressive member, and a resorbable material disposed within the least one space of the compressive member.

In accordance with a seventh embodiment of the present invention, a method of securing a bone member to an adjacent member is provided, comprising: (1) forming at least one bore in the bone member, (2) providing a bone screw, and (3) inserting the bone screw into the at least one bore. The bone screw includes a threaded surface on a distal portion thereof, the threaded surface having a first orientation, and a compressive member adjacent to the threaded surface, the compressive member having a second orientation opposite that of the first orientation, wherein the compressive member has an area defining at least one space between adjacent surfaces of the compressive member.

A more complete appreciation of the present invention and its scope can be obtained from the following detailed description of the invention, the drawings and the appended claims.

BRIEF DESCRIPTION OF THE DRAWINGS

The present invention will become more fully understood from the detailed description and the accompanying drawings, wherein.

The same reference numerals refer to the same parts throughout the various Figures.

DETAILED DESCRIPTION OF THE INVENTION

Figure 1:
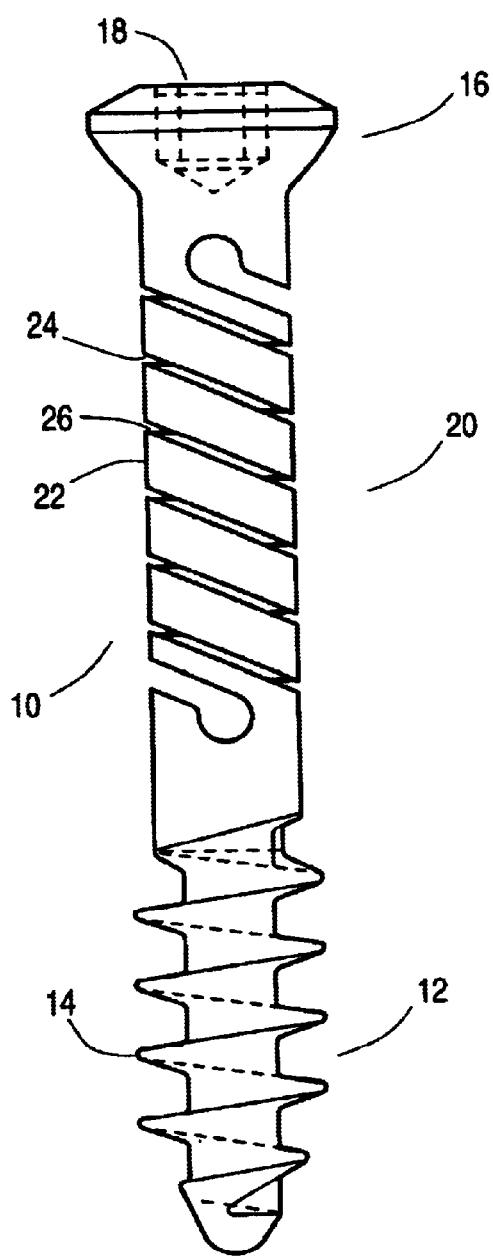
FIG. 1 is an elevational view of a bone screw in a relaxed state, in accordance with one embodiment of the present invention.

Referring to FIG. 1, there is shown a view of an illustrative design of a bone screw 10, in accordance with one embodiment of the present invention. The bone screw 10 is preferably comprised of a biocompatible material, such as stainless steel, titanium, cobalt-chrome alloys, and the like.

The bone screw 10 includes three primary portions. First, there is a distal portion 12 having a threaded surface 14 formed thereon by any number of conventional milling methods. It should be noted that the threaded surface 14 has a "right-hand" or turning (i.e., lathe) orientation; however, a "left-hand" orientation may also be used alternatively.

Next, there is a proximal head portion 16 having a recess 18 formed therein (by any number of conventional milling methods) for receiving a driving device, such as a hex driver, screw driver, or like device. Although the recess 18 is shown as being hex-shaped, it is envisioned that other configurations may be employed as well, such as different recess shapes or differently shaped males members to be engaged by a female drive mechanism.

Finally, there is an intermediate portion 20 having a compressive member 22, such as but not limited to a single or double helix, formed therein by any number of conventional methods, such as but not limited to wire electrical discharge machining (wire EPM). Moreover, while a double helix is shown, it should be understood that a single helix may also be employed or any other structure to achieve a compressive load or force.

It should also be noted that the compressive member 22 has an opposite or "left-hand" orientation as compared to the orientation of the threaded surface 14. Alternatively, if the threaded surface 14 has a "left-hand" orientation, the compressive member 22 would necessarily have to have a "right-hand" orientation, for the reasons to be discussed herein. Additionally, the diameter of the intermediate portion 20 is preferably less than the diameter of the threaded surface 14 so as not to interfere with the cutting function of the threads. Between each of the surfaces 24 of the compressive member 22 are areas defining spaces 26 where the adjacent surfaces 24 do not touch under normal circumstances. It should be noted that the bone screw 10, as shown, is in it's fully relaxed (i.e., unstressed) state.

Figure 2:
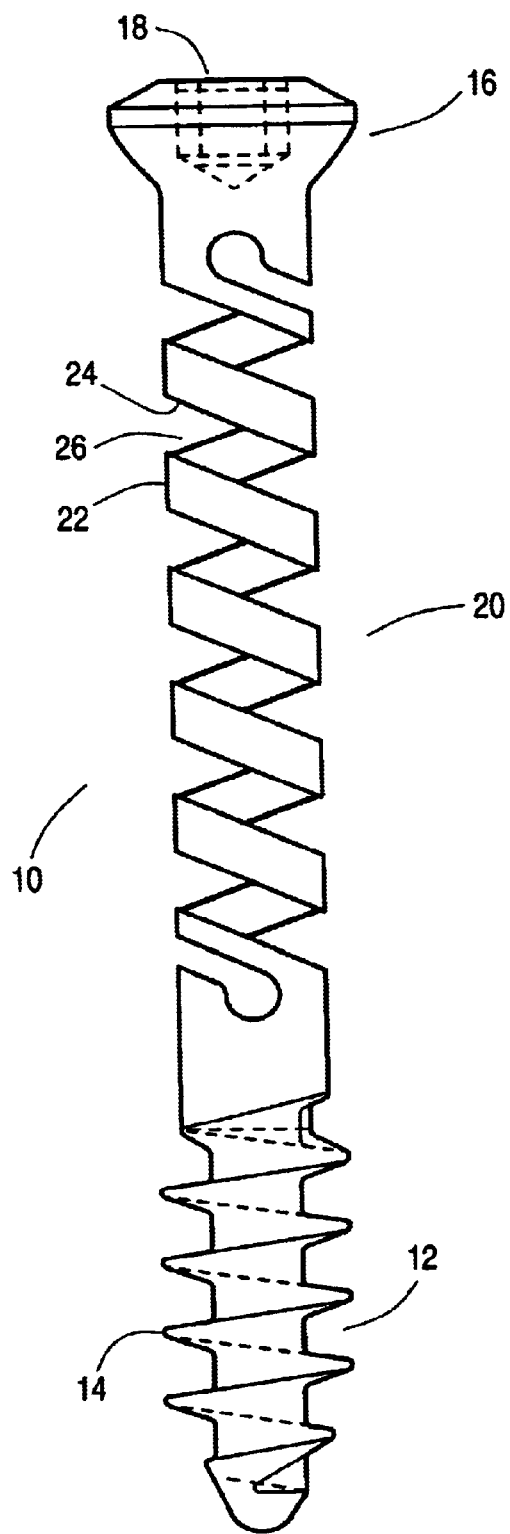
FIG. 2 is an elevational view of a bone screw in a stressed state, in accordance with one embodiment of the present invention.

Referring to FIG. 2, there is shown a view of the bone screw 10 depicted in FIG. 1 wherein the bone screw 10 is in it's fully stressed (i.e., unrelaxed) state. In this situation, the bone screw 10 is at the peak of it's tension level. In order to achieve this tension level in the bone screw 10, it is generally necessary to expand the length of the compressive member 22. This can be done in many different ways. By way of a non-limiting example, the distal portion 12 can be secured in a stationary chuck or similar device, while a hex driver or similar device rotates in the direction of the threaded surface 14 orientation, in this case, in a right-hand or clockwise direction. By doing so, the compressive member 22 portions "unwinds" or "expands" due to the fact that it is oriented in an opposite direction, that is in a left-hand or counter-clockwise direction, from the threaded surface 14. The result is that the spaces 26 between the respective surfaces 24 of the compressive member 22 have greatly increased in distance. Alternatively, an axial force could be applied to the compressive member 22 so as to "pull" the compressive member 22, thus further exposing the spaces 26 between the respective surfaces 24.

Figure 3:
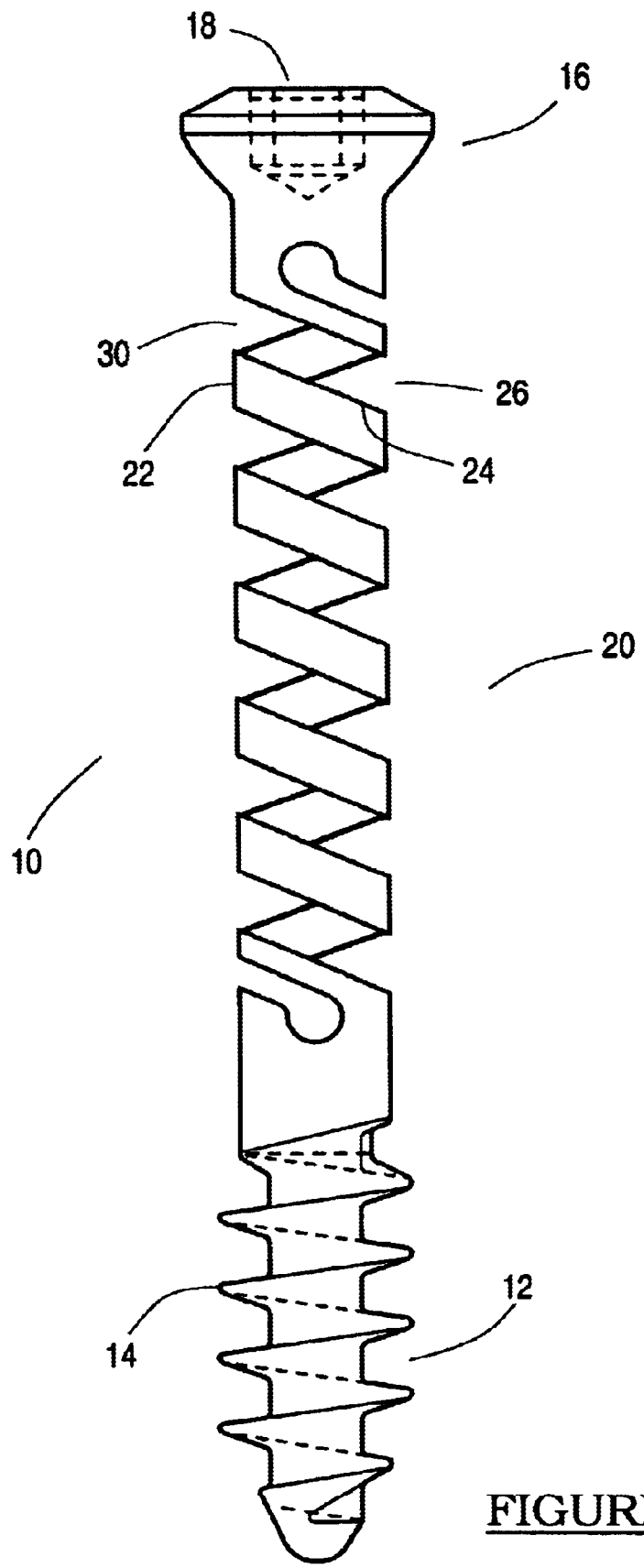
FIG. 3 is an elevational view of a bone screw in a stressed state with resorbable material disposed in the spaces between the surfaces of a helical coil, in accordance with one embodiment of the present invention.

Referring to FIG. 3, while the bone screw 10 remains in it's stressed state, it is appropriate to introduce a resorbable material 30 into the spaces 26 by any number of conventional methods. The use of various resorbable materials, typically in the form of various orthopedic devices, in connection with the treatment of various bone deformities, especially fractures, is fairly well known in the art. These resorbable materials, also referred to as bioresorbable, biodegradable, absorbable, and bioabsorbable devices, have enabled the medical community to achieve excellent surgical results, even under difficult clinical conditions.

The main benefit of using resorbable materials is that they are generally as strong as conventional metallic materials and resorb into the body over a generally predictable time period once a sufficient level of healing has occurred, for example, at the junction of a bone fracture, thus negating the need for subsequent removal of the material.

One resorbable material of particular interest is marketed by Biomet, Inc. (Warsaw, Indiana) under the tradename LACTOSORB®. LACTOSORB® is an absorbable co-polymer synthesized from all-natural ingredients: 82% L-lactic acid and 18% glycolic acid, unlike the homopolymers in common use such as 100% poly-L-lactic acid (PLLA) or 100% polyglycolic acid (PGA), LACTOSORB® copolymer is substantially amorphous (i.e., without crystallinity), meaning that its degradation is uniform, precluding the crystalline release associated with degrading copolymers that have been associated with late inflammatory reactions. Furthermore, the LACTOSORB® copolymer ratio permits the polymer to retain most of it's strength for six to eight weeks, which is appropriate for healing, but not so long as to raise concerns about long-term stress shielding of bone.

In accordance with a preferred embodiment of the present invention, the resorbable material 30 is comprised of polylactic acid, polyglycolic acid, and combinations thereof.

The resorbable material 30 is then allowed to cure and harden, so that when the bone screw 10 is released from whatever device is keeping it in it's stressed state, the bone screw 10 will not then relax and assume the configuration depicted in FIG. 1. The reason the bone screw 10 is unable to relax is that the cured resorbable material 30 is physically preventing the surfaces 24 of the compressive member 22 from moving towards one another.

The bone screw 10 containing the cured resorbable material 30 is now ready for use in the treatment of fractures, installation of implants and orthopedic appliances, or for any other suitable medical use.

Figure 4:
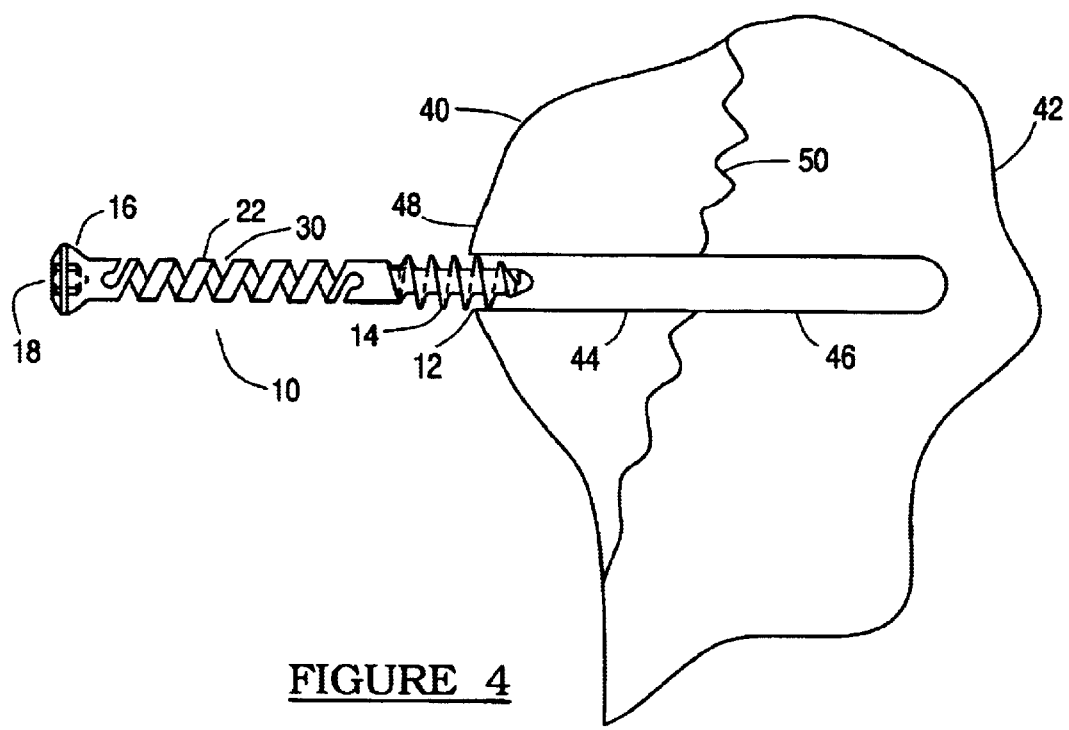
FIG. 4 is a partial sectional view of a bone screw being inserted into a proximal bore hole formed in a proximal bone fragment, in accordance with one embodiment of the present invention.
Figure 5:
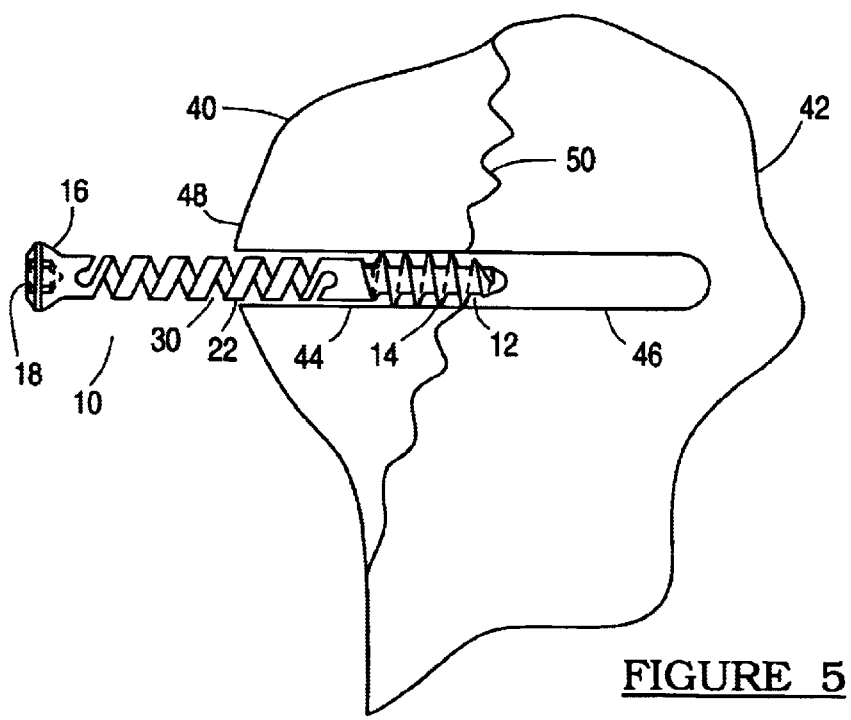
FIG. 5 is a partial sectional view of the bone screw depicted in FIG. 4 being inserted into a distal bore hole formed in a distal bone fragment, in accordance with one embodiment of the present invention.
Figure 6:
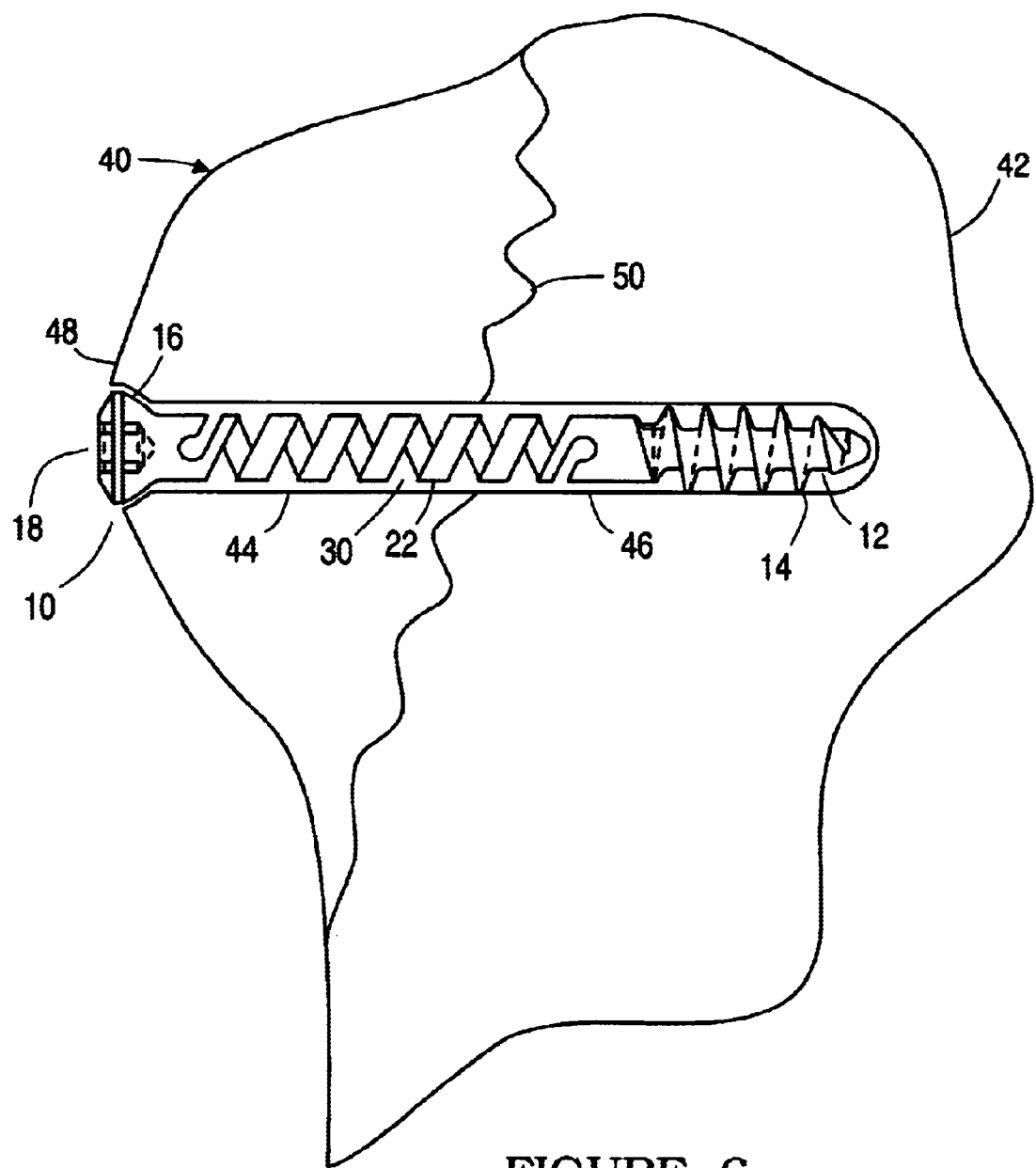
FIG. 6 is a partial sectional view of the bone screw depicted in FIGS. 4–5 being fully inserted into the distal bore hole formed in the distal bone fragment, in accordance with one embodiment of the present invention.

Referring to FIGS. 4–6, when it is desired to fasten or secure two or more bone fragments or members 40, 42 together, a pair of aligned bores 44, 46 (e.g., pilot holes) are preferably formed in the two bone fragments 40, 42, respectively. It should be noted that bore holes are not required, but are generally preferred. Thereupon, the bone screw 10 of the present invention (as generally shown in FIG. 3) is inserted into the first (i.e., proximal) bore 44, and a suitable tool, such as a hex driver (not shown), is inserted into the recess 18 to rotate the distal portion 12 in the same direction as the threaded surface 14 (i.e., right-hand or clockwise), which causes the rest of the bone screw 10 to rotate in the same direction. The present invention obviates the need for torque drivers, as the bone screw 10 will typically be able to easily penetrate bone tissue. With continued insertion of the bone screw 10, the distal portion 12 eventually enters and advances along the second (i.e., distal) bore 46 of the distal bone fragment 42. As the distal portion 12 continues to advance along the distal bore 46, the head portion 16 moves into engagement with (i.e., abuts) the outer surface 48 of the proximal bone fragment 40 such that continued advancement of the distal portion 12 is prohibited. It should be noted that continued rotation of the hex driver will not cause the compressive member 22 to relax and contract because the cured resorbable material 30 is holding it firmly in place.

At this point, the bone screw 10 contains it's maximum amount of initial tension, and is comparable to the amount of initial tension achieved with a conventional bone screw, which is substantially greater than the amount of initial tension contained in a conventional dynamic tension bone screw.

As the bone fragments 40, 42 undergo stress relaxation, the resorbable material 30 will gradually resorb at a predictable rate, allowing the compressive member 22 to relax while simultaneously exerting a tension force between the distal portion 12 and the proximal portion 16 of the screw 10 to thereby apply a corresponding compressive force on the bone fragments 40, 42. However, the rate of relaxation in the compressive member 22 is much slower than the rate of relaxation in the coil of a conventional dynamic tension bone screw because of the presence of the resorbable material 30 slowing the rate of relaxation. Thus, the actual tension exerted by the relaxing compressive member 22 actually remains fairly constant (with a very gradual drop-off) over time as the resorbable material 30 is slowly and uniformly resorbed. Thus, a greater amount of post-initial tension can be maintained between the bone fragments 40, 42 over a greater amount of time than would be possible with a conventional dynamic tension bone screw, thus allowing a longer period of time for the fracture to heal without the likelihood of failure of the fixation and eventual non-union or misalignment of the bone fragments 40, 42 at the fracture site 50.

Additionally, resorbable materials of differing resorbtion rates can be used to produce various rates and time periods of overall resorbtion. For example, a first resorbable material having a fast resorbtion rate can be disposed over a second resorbable material having a slow resorbtion rate, and vice versa, depending on the clinical needs to treat the fracture effectively.

Further, the bone screw 10 of the present invention can also be used in conjunction with the installation of various types of orthopedic implants and orthopedic appliances, such as bone plates, acetabular cups, tibial base plates, glenoids, and the like. In both of these cases, it is typically necessary to only provide a single bore or pilot hole for insertion of the bone screw 10, as opposed to using two separate bore holes for treating bone fractures. Again, as the surrounding bone tissue undergoes stress relaxation, the resorbable material 30 will gradually resorb at a predictable rate, allowing the compressive member 22 to relax while simultaneously exerting a tension force between the distal portion 12 and the proximal portion 16, thus preventing, or at least lessening, the risk of failure at the implant or appliance site.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. A bone screw, comprising:
    a distal portion having a threaded surface thereon, the threaded surface having a first orientation;
    a proximal portion;
    an intermediate portion comprising a compressive member integral with said distal and proximal portions, the compressive member having a second orientation opposite that of the first orientation; and
    a resorbable material is disposed within a space of the compressive member when the compressive member is in a stressed state.

2. The bone screw according to claim 1, wherein the compressive member comprises a single helix.

3. The bone screw according to claim 1, wherein the compressive member comprises a double helix.

4. The bone screw according to claim 1, wherein the compressive member has an area defining at least one space between adjacent surfaces of the compressive member.

5. The bone screw according to claim 1, wherein the resorbable material is allowed to cure within the space of the compressive member when the compressive member is in a stressed state.

6. The bone screw according to claim 1, wherein the resorbable material is comprised of materials selected from the group consisting of polylactic acid, polyglycolic acid, and combinations thereof.

7. A bone screw, comprising:
    a distal portion having a threaded bone engaging surface thereon;
    a proximal head portion configured to mate with an insertion tool;
    an intermediate portion comprising a compressive member integral with said distal and proximal portions, the compressive member having an area defining at least one space between adjacent surfaces of the compressive member; and
    a resorbable material disposed within the at least one space of the compressive spring member, wherein the resorbable material is disposed within the space of the compressive member when the compressive member is in a stressed state.

8. The bone screw according to claim 7, wherein the compressive member comprises a single helix.

9. The bone screw according to claim 7, wherein the compressive member comprises a double helix.

10. The bone screw according to claim 7, wherein the resorbable material is allowed to cure within the least one space of the compressive member when the compressive member is in a stressed state.

11. The bone screw according to claim 7, wherein the resorbable material is comprised of materials selected from the group consisting of polylactic acid, polyglycolic acid, and combinations thereof.

12. A method of securing a bone member to an adjacent member, comprising:
    forming at least one bore in the bone member;
    providing a bone screw;
    inserting the bone screw into the at least one bore;
    wherein the bone screw includes a threaded surface on a distal portion thereof, the threaded surface having a first orientation;
    wherein the bone screw includes a compressive member adjacent to the threaded surface, the compressive member having a second orientation opposite that of the first orientation, the compressive member having an area defining at least one space between adjacent surfaces of the compressive member;
    wherein the bone screw includes a resorbable material disposed within the space of the compressive member when the compressive member is in a stressed state.

13. The method according to claim 12, wherein the compressive member comprises a single helix.

14. The method according to claim 13, wherein the adjacent member is selected from the group consisting of another bone member, an orthopedic implant, an orthopedic appliance, and combinations thereof.

15. The method according to claim 13, further comprising at least one other bore formed in the adjacent member.

16. The method according to claim 15, wherein the bone screw is inserted into the at least one other bore.

17. The method according to claim 15, wherein the at least one bore and the at least one other bore are substantially aligned.

18. The method according to claim 12, wherein the compressive member comprises a double helix.

* * * * *

UNITED STATES PATENT AND TRADEMARK OFFICE
CERTIFICATE OF CORRECTION

PATENT NO. : 6,656,184 B1
DATED : December 2, 2003
INVENTOR(S) : John R. White and Jeffrey C. King It is certified that error appears in the above-identified patent and that said Letters Patent is hereby corrected as shown below:

Title page,
Item [56], References Cited, FOREIGN PATENTS DOCUMENTS, also list: -- SU 1181652 9/1985 --.

Column 1,
Line 35, "bone:" should be -- bone --.

Column 2,
Line 61, after first occurrence of "the" insert -- at --.

Column 3,
Lines 16 and 29, after first occurrences of "the" insert -- at --.

Column 4,
Line 32, "males" should be -- male --.
Lines 55, 58 and 59, "it's" should be -- its --.

Column 5,
Lines 11, 39 and 48, "it's" should be -- its --.

Column 6,
Line 16, "it's" should be -- its --.

Column 8,
Line 8, after "the" insert -- at --.

Signed and Sealed this

Eleventh Day of January, 2005

JON W. DUDAS
*Director of the United States Patent and Trademark Office*